(12) United States Patent
Kinoshita et al.

(10) Patent No.: US 7,871,613 B2
(45) Date of Patent: Jan. 18, 2011

(54) ADJUVANT THERAPY WITH THE USE OF ANTI-GLYPICAN 3 ANTIBODY

(75) Inventors: Yasuko Kinoshita, Kanagawa (JP); Masamichi Sugimoto, Kanagawa (JP); Hisafumi Okabe, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 174 days.

(21) Appl. No.: 11/574,091

(22) PCT Filed: Aug. 23, 2005

(86) PCT No.: PCT/JP2005/015607
§ 371 (c)(1),
(2), (4) Date: Jun. 11, 2007

(87) PCT Pub. No.: WO2006/022407
PCT Pub. Date: Mar. 2, 2006

(65) Prior Publication Data
US 2007/0269444 A1    Nov. 22, 2007

(30) Foreign Application Priority Data
Aug. 24, 2004  (JP)  .............. 2004-244273
Mar. 28, 2005  (JP)  .............. 2005-090945

(51) Int. Cl.
*A61K 39/395* (2006.01)
*A61K 39/00* (2006.01)
*C07K 16/00* (2006.01)
*C12P 21/08* (2006.01)

(52) U.S. Cl. ............... 424/130.1; 424/133.1; 424/138.1; 424/141.1; 530/387.1; 530/387.3; 530/387.7; 530/388.1

(58) Field of Classification Search ........................ None
See application file for complete search history.

(56) References Cited

U.S. PATENT DOCUMENTS

| | | | |
|---|---|---|---|
| 5,530,101 | A | 6/1996 | Queen et al. |
| 6,165,745 | A | 12/2000 | Ward et al. |
| 6,210,670 | B1 | 4/2001 | Berg |
| 6,737,056 | B1 | 5/2004 | Presta |
| 7,297,775 | B2 | 11/2007 | Idusogie et al. |
| 7,361,336 | B1 | 4/2008 | Bergstein |
| 7,427,400 | B2 | 9/2008 | Bergstein |
| 2004/0024320 | A1 | 2/2004 | Karasawa et al. |
| 2004/0236080 | A1 | 11/2004 | Aburatani et al. |
| 2005/0171339 | A1 | 8/2005 | Sugo et al. |
| 2005/0233392 | A1 | 10/2005 | Filmus et al. |
| 2006/0024298 | A1 | 2/2006 | Lazar et al. |
| 2006/0040325 | A1 | 2/2006 | Wu et al. |
| 2006/0167232 | A1 | 7/2006 | Aburatani et al. |
| 2006/0188510 | A1 | 8/2006 | Aburatani et al. |
| 2006/0287508 | A1 | 12/2006 | Sugo et al. |
| 2007/0087005 | A1 | 4/2007 | Lazar et al. |
| 2007/0172488 | A1 | 7/2007 | Aburatani et al. |
| 2007/0190599 | A1 | 8/2007 | Nakano et al. |
| 2008/0008710 | A1 | 1/2008 | Aburatani et al. |
| 2008/0051563 | A1 | 2/2008 | Lazar et al. |
| 2008/0124330 | A1 | 5/2008 | Nakano et al. |
| 2008/0154025 | A1 | 6/2008 | Lazar et al. |
| 2008/0161541 | A1 | 7/2008 | Lazar et al. |
| 2008/0181890 | A1 | 7/2008 | Lazar et al. |
| 2008/0267979 | A1 | 10/2008 | Lazar et al. |

FOREIGN PATENT DOCUMENTS

| | | |
|---|---|---|
| EP | 1 176 195 | 1/2002 |
| EP | 1 331 266 | 7/2003 |
| EP | 1 411 118 | 4/2004 |
| EP | 1 462 799 | 9/2004 |
| EP | 1 464 702 | 10/2004 |
| EP | 1 498 491 | 1/2005 |
| EP | 1548 442 | 6/2005 |
| EP | 1541680 | 6/2005 |
| EP | 1 561 686 | 8/2005 |
| EP | 1 671 645 | 6/2006 |
| EP | 1 674 111 | 6/2006 |
| EP | 1 800 693 | 6/2007 |

(Continued)

OTHER PUBLICATIONS

Midorikawa, Ishikawa, Iwanari, Imamura, Sakamoto, Miyazono, Kodama, Makuuchi, and Aburatani. Glypican 3, overexpressed in hepatocellular carcinoma, modulates FGF2, and BMP-7 signaling. International Journal of Cancer, 2003. vol. 103, pp. 455-465.*
MSNBC News Services. Mixed results on new cancer drug. 2000.*
Gura. Systems for identifying new drugs are often faulty. Science, 1997. vol. 278, pp. 1041-1042.*
Jiang, Yang, and Hu. Recurrence of metastasis of HCC: predictors, early detection, and experimental antiangiogenic therapy. World Journal of Gastroenterology, 2000. vol. 6, pp. 61-65.*
Capurro, Wanless, Sherman, Deboer, Shi, Miyoshi, and Filmus. Glypcian-3: a novel serum and histochemical marker for hepatocellular carcinoma. Gastroenterology, 2003. vol. 125, pp. 89-97.*

(Continued)

*Primary Examiner*—Anne M. Gussow
(74) *Attorney, Agent, or Firm*—Fish & Richardson P.C.

(57) ABSTRACT

The present invention provides an anti-cancer agent comprising anti-glypican 3 antibody wherein the anti-cancer agent is administered after a cancer treatment, Preferably, after a cancer treatment is after a treatment for liver cancer, and the treatment for liver cancer is in particular a resection of liver cancer cells. The anti-cancer agent according to the present invention is preferably administered if glypican 3 is expressed in the resected liver cancer cells. The anti-glypican 3 antibody is preferably a monoclonal antibody. The anti-cancer agent according to the present invention is useful for preventing cancer and for preventing the recurrence of cancer.

20 Claims, 1 Drawing Sheet

FOREIGN PATENT DOCUMENTS

| | | |
|---|---|---|
| EP | 1 816 140 | 8/2007 |
| JP | 2-42355 | 2/1990 |
| JP | 4-336051 | 11/1992 |
| JP | 11-118775 | 4/1999 |
| JP | 2001-108661 | 4/2001 |
| JP | 2002-48867 | 2/2002 |
| JP | 2003-149213 | 5/2003 |
| JP | 2004-053360 | 2/2004 |
| WO | WO9322332 | 11/1993 |
| WO | WO9823289 | 6/1998 |
| WO | WO 99/54342 | 10/1999 |
| WO | WO 00/61739 | 10/2000 |
| WO | WO 02/22739 | 3/2002 |
| WO | WO 02/31140 | 4/2002 |
| WO | WO 02/079255 | 10/2002 |
| WO | WO 03/000883 | 1/2003 |
| WO | WO 03/042686 | 5/2003 |
| WO | WO 03/057881 | 7/2003 |
| WO | WO 03/074679 | 9/2003 |
| WO | WO 03/085119 | 10/2003 |
| WO | WO 03/100429 | 12/2003 |
| WO | WO 2004/018667 | 3/2004 |
| WO | WO 2004/022597 | 3/2004 |
| WO | WO 2004/022739 | 3/2004 |
| WO | WO 2004/022754 | 3/2004 |
| WO | WO 2004/023145 | 3/2004 |
| WO | WO 2004/038420 | 5/2004 |
| WO | WO 2004/099249 | 11/2004 |
| WO | WO 2005/023301 | 3/2005 |
| WO | WO 2006/006693 | 1/2006 |
| WO | WO 2006/022407 | 3/2006 |
| WO | WO 2006/046751 | 5/2006 |
| WO | WO 2007/047291 | 4/2007 |

OTHER PUBLICATIONS

Midorikawa, Ishikawa, Iwanari, Imamura, Sakamoto, Miyazono, Kodama, Makuuchi, and Aburatani. Glypican-3, overexpressed in hepatocellular carcinoma, modulates FGF2 and BMP-7 signaling. International Journal of Cancer, 2003. vol. 103, pp. 455-465.*

Hippo, Watanabe, Midorikawa, Yamamoto, Ihara, Tokita, Iwanari, Ito, Nakano, Nezu, Tsunoda, Yoshino, Ohizumi, Tsuchiya, Ohnishi, Makuuchi, Hamakubo, Kodama, and Aburatani. Identification of soluble NH2-terminal fragment of glypican-3 as a serological marker for early stage hepatocellular carcinoma. Cancer Research, 2004. vol. 64, p. 2418-2423.*

Rudikoff, Giusti, Cook, and Scharff. Single amino acid substitution altering antigen-binding specificity. Proceedings of the National Academy of Sciences, 1982. vol. 79, pp. 1979-1983.*

Mac Callum, Martin, and Thornton. Antibody-antigen interactions: contact analysis and binding site topography. Journal of Molecular Biology, 1996. vol. 262, pp. 732-745.*

De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanized monoclonal antibody. Journal of Immunology, 2002. vol. 169, pp. 3076-3084.*

Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*

Vajdos, Adams, Breece, Presta, De Vos, and Sidhu. Comprehensive functional maps of the antigen binding site of an anti-ErbB2 antibody obtained by shotgun scanning mutagenesis. Journal of Molecular Biology, 2002. vol. 320, pp. 415-428.*

Holm, Jafari, Sundstrom. Functional mapping and single chain construction of anti-cytokeratin 8 monoclonal antibody TS1. Molecular Immunology, 2007. vol. 44, pp. 1075-1084.*

Chen, Wiesmann, Fuh, Li, Christinger, Mc Kay, De Vos, and Lowman. Selection and analysis of an optimized anti-VEGF antibody: crystal structure of an affinity-matured Fab in complex with antigen. Journal of Molecular Biology, 1999. vol. 293, pp. 865-881.*

Wu, Nie, Huse, and Watkins. Humanization of a murine monoclonal antibody by simultaneous optimization of framework and CDR residues. Journal of Molecular Biology, 1999. vol. 294, pp. 151-162.*

Sung et al., "Glypican-3 is overexpressed in human hepatocellular carcinoma," Cancer Sci., 94:259-262 (2003).

Yamaguchi et al., "Current Status and Future Perspective of Biotherapy for Cancer," Biotherapy, 13:747-753 (1999) (English summary included).

Carter, "Improving the efficacy of antibody-based cancer therapies," Nat. Rev. Cancer, 1:118-129 (2001).

Nakatsura et al., "Glypican-3, overexpressed specifically in human hepatocellular carcinoma, is a novel tumor marker," Biochem. Biophys. Res. Commun., 306:16-25 (2003).

Abe et al., "Matrixeye™ Portable 3D Ultrasonic Inspection System," Toshiba Review, 60:48-51 (2005).

Arii et al., "Characteristics of recurrent hepatocellular carcinoma in Japan and our surgical experience," J. Hepatobiliary Pancrea. Surg. 8:397-403 (2001).

Bendayan, "Possibilities of False Immunocytochemical Results Generated by the Use of Monoclonal Antibodies: The Example of the Anti-Proinsulin Antibody," J. Histochem. Cytochem., 43(9):881-886 (1995).

Bost et al., "Antibodies Against a Peptide Sequence within the HIV Envelope Protein Crossreacts with Human Interleukin-2," Immunol. Invest., 17:577-586 (1988).

Brorson et al., "Mutational Analysis of Avidity and Fine Specificity of Anti-Levan Antibodies," J Immunol., 163:6694-6701 (1999).

Brummell et al., "Probing the combining site of an anti-carbohydrate antibody by saturation-mutagenesis: role of the heavy-chain CDR3 residues," Biochemistry, 32:1180-87 (1993).

Budhu et al., "The Molecular Signature of Metastases of Human Hepatocellular Carcinoma," Oncology, 69(suppl 1):23-27 (2005).

Burks et al., "In vitro scanning saturation mutagenesis of an antibody binding pocket," Proc. Natl. Acad. Sci. USA, 94:412-417 (1997).

Cappuro et al., "Overexpression of Glypican-3 in Human Hepatocellular Carcinomas Determined by Immunohistochemistry Using a Monocolonal Antibody," Proceedings of the Annual Meeting of the American Association for Cancer Research, 93$^{rd}$ Annual Meeting, Apr. 6-10, 2002, 43:219 Abstract #1097 (2002).

Casset et al., "A peptide mimetic of an anti-CD4 monoclonal antibody by rational design," Biochem. Biophys. Res. Commun., 307:198-205 (2003).

Chen et al., "Selection and Analysis of an Optimized Anti-VEGF Antibody: Crystal Structure of an Affinity-Matured Fab in Complex with Antigen," J. Mol. Biol., 293:865-881 (1999).

Colman, "Effects of amino acid sequence changes on antibody-antigen interactions," Res. Immunol., 145:33-36 (1994).

De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," J. Immunol., 169:3076-84 (2002).

Dennis, "Cancer: Off by a whisker," Nature, 442:739-741 (2006).

Dufner et al., "Harnessing phage and ribosome display for antibody optimization," Trends Biotechnol., 24:523-529 (2006).

Filmus, "Glypicans in Growth Control and Cancer," Glycobiology, 11:19R-23R (2001).

Gonzalez et al. "OCI-5/GPC3, A Glypican Encoded by a Gene That is Mutated in the Simpson-Golabi-Behmel Overgrowth Syndrome, Induces Apoptosis in a Cell Line-Specific Manner," J. Cell Biol., 141:1407-14 (1998).

Holm et al., "Functional mapping and single chain construction of the anti-cytokeratin 8 monoclonal antibody TS1," Mol. Immunol., 44:1075-84 (2007).

Huber, "Structure and Function of the Human Glypican 3 Gene," Washington University, Division of Biology and Biomedical Sciences Program in Molecular Genetics, St. Louis, Missouri (Dec. 1998).

Jang et al., "The structural basis for DNA binding by an anti-DNA autoantibody," *Mol. Immunol.*, 35:1207-1217 (1998).

Kobayashi et al., "Tryptophan H33 plays an important role in pyrimidine (6-4) pyrimidone photoproduct binding by a high-affinity antibody," *Protein Eng.*, 12:879-884 (1999).

Kumar et al., "Molecular Cloning and Expression of the Fabs of Human Autoantibodies in *Escherichia coli*," *J. Biol. Chem.*, 275:35129-36 (2000).

Lage et al. "Cloning and Characterization of Human cDNAs Encoding a Protein with High Homology to Rat Intestinal Development Protein OCI-5," *Gene*, 188:151-156 (1997).

Lage et al. "Expression of a Glypican-Related 62-kDa Antigen is Decreased in Hepatocellular Carcinoma in Correspondence to the Grade of Tumor Differentiation," *Virchows Arch*, 438:567-573 (2001).

Lund et al., "Multiple interactions of IgG with its core oligosaccharide can modulate recognition by complement and human Fcγ receptor I and influence the synthesis of its oligosaccharide chains," *J. Immunol.*, 157:4963-69 (1996).

Maccallum et al., "Antibody-antigen Interactions: Contact Analysis and Binding Site Topography," *J. Mol. Biol.*, 262:732-745 (1996).

Man et al., "Upregulation of Glypican-3 Expression in Hepatocellular Carcinoma but Downregulation in Cholangiocarcinoma Indicates its Differential Diagnosis Value in Primary Liver Cancers," *Liver Int.*, 25:962-966 (2005).

Niwa et al., "Defucosylated Chimeric Anti-CC Chemokine Receptor 4 IgG1 with Enhanced Antibody-Dependent Cellular Cytotoxicity Shows Potent Therapeutic Activity to T-Cell Leukemia and Lymphoma," *Cancer Res.*, 64:2127-33 (2004).

Pilia et al. "Mutations in GPC3, A Glypican Gene, Cause the Simpson-Golabi-Behmel Overgrowth Syndrome," *Nat. Genet.*, 12:241-247 (1996).

Presta, LG, "Engineering Antibodies for Therapy," *Curr. Pharm. Biotechnol.*, 3:237-356 (2002).

Roskams et al., "Heparan sulphate proteoglycan expression in human primary liver tumours," *J. Pathol.*, 185:290-297 (1998).

Rudikoff et al., "Single amino acid substitution altering antigen-binding specificity," *Proc. Natl. Acad. Sci. USA*, 79:1979-83 (1982).

Sabit et al., "Enhanced expression of basement-membrane-type heparan sulfate proteoglycan in tumor fibro-myxoid stroma of intrahepatic cholangiocarcinoma," *Pathol. Int.*, 51:248-256 (2001).

Seaver, "Monoclonal Antibodies in Industry: More Difficult Than Originally Thought," *Genet. Eng.*, 14:10, 21 (1994).

Shields et al., "Lack of Fucose on Human IgG1 N-Linked Oligosaccharide ImproveS Binding to Human Fcgamma RIII and Antibody-dependent Cellular Toxicity," *J. Biol. Chem.*, 277:26733-40 (2002).

Shinkawa et al., "The absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," *J. Biol. Chem.*, 278:3466-73 (2003).

Smith-Gill et al., "Contributions of immunoglobulin heavy and light chains to antibody specificity for lysozyme and two haptens," *J. Immunol.*, 139:4135-44 (1987).

Song et al., "Light Chain of Natural Antibody Plays a Dominant Role in Protein Antigen Binding," *Biochem. Biophys. Res. Commun.*, 268:390-394 (2000).

Steplewski et al., Biological activity of human-mouse IgG1, IgG2, IgG3, and IgG4 chimeric monoclonal antibodies with antitumor specificity, *Proc. Natl. Acad. Sci. USA*, 85:4852-56 (1988).

Tang et al., "Metastatic human hepatocellular carcinoma models in nude mice and cell line with metastatic potential," *World J. Gastroenterol.*, 7:597-601 (2001).

Vajdos et al., "Comprehensive Functional Maps of the Antigen-binding Site of an Anti-ErbB2 Antibody Obtained with Shotgun Scanning Mutagenesis," *J. Mol. Biol.*, 320:415-428 (2002).

Voskoglou-Nomikos et al., "Clinical Predictive Value of the In Vitro Cell Line, Human Xenograft, and Mouse Allograft Preclinical Cancer Models," *Clin. Cancer Res.*, 9:4227-39 (2003).

Yamane-Ohnuki et al., "Establishment of *FUT8* Knockout Chinese Hamster Ovary Cells: An Ideal Host Cell Line for Producing Completely Defucosylated Antibodies With Enhanced Antibody-Dependent Cellular Cytotoxicity,"*Biotechnol Bioeng.*, 87:614-622 (2004).

Wichert et al., "Glypican-3 is involved in cellular protection against mitoxantrone in gastric carcinoma cells," *Oncogene*, 23:945-955 (2004).

Wu et al., "Humanization of a Murine Monoclonal Antibody by Simultaneous Optimization of Framework and CDR Residues," *J. Mol. Biol.*, 294:151-162 (1999).

USPTO Restriction Requirement in U.S. Appl. No. 11/251,561, dated Dec. 13, 2007, 9 pages.

Fish & Richardson P.C., Response to Restriction Requirement dated Dec. 13, 2007 in U.S. Appl. No. 11/251,561, filed Feb. 12, 2008, 1 page.

USPTO Office Action in U.S. Appl. No. 11/251,561, dated May 14, 2008, 12 pages.

Fish & Richardson P.C., Amendment in Reply to Action dated May 14, 2008 in U.S. Appl. No. 11/251,561, filed Nov. 13, 2008, 8 pages.

USPTO Final Office Action in U.S. Appl. No. 11/251,561, dated Feb. 25, 2009, 13 pages.

International Search Report and Written Opinion for App. Ser. No. PCT/US2006/039682 dated Apr. 13, 2007, 13 pages.

USPTO Restriction Requirement in U.S. Appl. No. 10/583,795, dated Dec. 18, 2007, 5 pages.

Fish & Richardson P.C., Response to Restriction Requirement dated Dec. 18, 2007 in U.S. Appl. No. 10/583,795, filed Jan. 18, 2008, 19 pages.

USPTO Office Action in U.S. Appl. No. 10/583,795, dated Mar. 27, 2008, 42 pages.

Fish & Richardson P.C., Amendment in Reply to Action dated Mar. 27, 2008 in U.S. Appl. No. 10/583,795, filed Sep. 29, 2008, 46 pages.

USPTO Office Action in U.S. Appl. No. 10/583,795, dated Jan. 7, 2009, 25 pages.

Interview Summary in U.S. Appl. No. 10/583,795, dated Apr. 8, 2009, 2 pages.

Fish & Richardson P.C., Amendment in Reply to Action dated Jan. 7, 2009 in U.S. Appl. No. 10/583,795, filed Apr. 7, 2009, 13 pages.

Interview Summary in U.S. Appl. No. 10/583,795, dated Apr. 20, 2009, 2 pages.

USPTO Office Action in U.S. Appl. No. 10/583,795, dated Jun. 26, 2009, 19 pages.

Fish & Richardson P.C., Amendment in Reply to Action dated Jun. 26, 2009 in U.S. Appl. No. 10/583,795, filed Dec. 24, 2009, 17 pages.

International Search Report for Appl. Ser. No. PCT/JP2005/013103, mailed Oct. 25, 2005, 1 page.

International Preliminary Report on Patentability for App. Ser. No. PCT/JP2005/013103, dated Jan. 7, 2009, 4 pages.

European Search Report for App. Ser. No. EP 05 76 0156, dated Oct. 1, 2007, 15 pages.

USPTO Restriction Requirement in U.S. Appl. No. 10/570,647, dated Apr. 4, 2008, 6 pages.

International Search Report for App. Ser. No. PCT/JP2004/013183, mailed Nov. 30, 2004, 4 pages.

International Preliminary Report on Patentability for App. Ser. No. PCT/JP2004/013183, dated Sep. 1, 2005, 17 pages.

European Search Report for App. Ser. No. EP 04 77 2 922, dated Jun. 14, 2007, 2 pages.

USPTO Office Action in U.S. Appl. No. 11/577,944, dated Apr. 28, 2009, 14 pages.

Fish & Richardson P.C., Amendment in Reply to Office Action dated Apr. 28, 2009 in U.S. Appl. No. 11/577,944, filed Oct. 27, 2009, 15 pages.

USPTO Final Office Action in U.S. Appl. No. 11/577,944, dated Jan. 20, 2010, 47 pages.

International Search Report for U.S. Appl. No. PCT/JP2005/020057, mailed Jan. 24, 2006, 2 pages.

European Search Report for App. Ser. No. EP 05 80 0031, dated Jul. 31, 2009, 9 pages.

Search Report and Written Opinion for App. Ser. No. SG 200703074-5, mailed Jul. 21, 2008, 9 pages.

International Search Report for App. Ser. No. PCT/JP2005/015607, mailed Oct. 24, 2005, 3 pages.

European Search Report for App. Ser. No. EP 05 78 0979, dated Nov. 10, 2008, 5 pages.

USPTO Restriction Requirement in U.S. Appl. No. 10/526,741, dated Mar. 27, 2006, 5 pages.

Davidson, Davidson & Kappel, LLC, Response to Restriction Requirement dated Mar. 27, 2006 in U.S. Appl. No. 10/526,741, filed Apr. 25, 2006, 6 pages.
USPTO Office Action in U.S. Appl. No. 10/526,741, dated Jun. 14, 2006, 40 pages.
Davidson, Davidson & Kappel, LLC, Amendment in Reply to Office Action dated Jun. 14, 2006 in U.S. Appl. No. 10/526,741, filed Dec. 12, 2006, 18 pages.
USPTO Final Office Action in U.S. Appl. No. 10/526,741, dated Mar. 9, 2007, 17 pages.
Davidson, Davidson & Kappel, LLC, Amendment in Reply to Office Action dated Mar. 9, 2007 in U.S. Appl. No. 10/526,741, filed Jul. 9, 2007, 9 pages.
USPTO Advisory Action in U.S. Appl. No. 10/526,741, dated Aug. 14, 2007, 3 pages.
Davidson, Davidson & Kappel, LLC, Amendment in Reply to Action dated Aug. 14, 2007 in U.S. Appl. No. 10/526,741, filed Sep. 6, 2007, 9 pages.
USPTO Office Action in U.S. Appl. No. 10/526,741, dated Nov. 21, 2007, 17 pages.
Davidson, Davidson & Kappel, LLC, Amendment in Reply to Action dated Nov. 21, 2007 in U.S. Appl. No. 10/526,741, filed Mar. 20, 2008, 10 pages.
USPTO Final Office Action in U.S. Appl. No. 10/526,741, dated Jul. 9, 2008, 11 pages.
Davidson, Davidson & Kappel, LLC, Amendment in Reply to Office Action dated Jul. 9, 2008 in U.S. Appl. No. 10/526,741, filed Jan. 5, 2009, 113 pages.
USPTO Advisory Action in U.S. Appl. No. 10/526,741, dated Jan. 21, 2009, 4 pages.
USPTO Office Action in U.S. Appl. No. 10/526,741, dated Sep. 1, 2009, 15 pages.
Davidson, Davidson & Kappel, LLC, Amendment in Reply to Office Action dated Sep. 1, 2009 in U.S. Appl. No. 10/526,741, filed Feb. 24, 2010, 10 pages.
USPTO Office Action in U.S. Appl. No. 10/481,524, dated Apr. 3, 2006, 23 pages.
Davidson, Davidson & Kappel, LLC, Amendment in Reply to Office Action dated Apr. 3, 2006 in U.S. Appl. No. 10/481,524, filed Aug. 31, 2006, 9 pages.
USPTO Interview Summary in U.S. Appl. No. 10/481,524, dated Sep. 6, 2006, 3 pages.
USPTO Restriction Requirement in U.S. Appl. No. 10/481,524, Jan. 5, 2007, 4 pages.
USPTO Office Communication in U.S. Appl. No. 10/481,524, Jan. 23, 2007, 2 pages.
USPTO Restriction Requirement in U.S. Appl. No. 11/702,780, dated Jul. 24, 2007, 5 pages.
Davidson, Davidson & Kappel, LLC, Response to Restriction Requirement dated Jul. 24, 2007 in U.S. Appl. No. 11/702,780, filed Aug. 22, 2007, 4 pages.
USPTO Office Action in U.S. Appl. No. 11/702,780, dated Nov. 16, 2007, 9 pages.
USPTO Interview Summary in U.S. Appl. No. 11/702,780, dated Dec. 14, 2007, 4 pages.
Davidson, Davidson & Kappel, LLC, Amendment in Reply to Office Action dated Nov. 16, 2007 in U.S. Appl. No. 11/702,780, filed May 16, 2008, 11 pages.
USPTO Office Action in U.S. Appl. No. 11/702,780, dated Sep. 3, 2008, 9 pages.
Davidson, Davidson & Kappel, LLC, Amendment in Reply to Office Action dated Sep. 3, 2008 in U.S. Appl. No. 11/702,780, filed Dec. 29, 2008, 6 pages.
USPTO Advisory Action in U.S. Appl. No. 11/702,780, dated Jan. 13, 2009, 4 pages.
USPTO Office Action in U.S. Appl. No. 11/702,780, dated Apr. 2, 2009, 7 pages.
Davidson, Davidson & Kappel, LLC, Amendment in Reply to Office Action dated Apr. 2, 2009 in U.S. Appl. No. 11/702,780, filed Sep. 30, 2009, 215 pages.
USPTO Notice of Allowance in U.S. Appl. No. 11/702,780, dated Jan. 26, 2010, 5 pages.
Ghetie et al., "Multiple Roles for the Major Histocompatibility Complex Class I-Related Receptor FcRn," Annu. Rev. Immunol., 18:739-766 (2000).
Hinton et al,. "Engineered Human IgG Antibodies with Longer Serum Half-lives in Primates," J. Biol. Chem., 279:6213-16 (2004).
Kim et al., "Mapping the site on human IgG for binding of the MHC class I-related receptor, FcRn," Eur. J. Immunol., 29:2819-25 (1999).
Martin et al., "Crystal Structure at 2.8 Å of an FcRn/Heterodimeric Fc Complex: Mechanism of pH-Dependent Binding," Mol. Cell, 7:867-877 (2001).
Medesan et al., "Delineation of the Amino Acid Residues Involved in Transcytosis and Catabolism of Mouse IgG1," J. Immunol., 158:2211-17 (1997).
Raghavan et al., "Fc Receptors and their Interactions with Immunoglobulins," Annu. Rev. Cell Dev. Biol., 12:181-220 (1996).
USPTO Notice of Allowance in U.S. Appl. No. 10/583,795, dated Mar. 10, 2010, 16 pages.
Fish & Richardson P.C., Reply to Action dated Feb. 25, 2009 in U.S. Appl. No. 11/251,561, filed Mar. 24, 2010, 4 pages.

* cited by examiner

ADJUVANT THERAPY WITH THE USE OF ANTI-GLYPICAN 3 ANTIBODY

CROSS-REFERENCE TO RELATED APPLICATIONS

This application is the National Stage of International Application No. PCT/JP2005/015607, filed on Aug. 23, 2005, which claims the benefit of Japanese Patent Application Serial No. 2004-244273, filed on Aug. 24, 2004, and Japanese Patent Application Serial No. 2005-090945, filed on Mar. 28, 2005. The contents of all of the preceding applications are hereby incorporated by reference in their entireties.

TECHNICAL FIELD

The present invention relates to adjuvant therapy following a cancer treatment, in which the adjuvant therapy utilizes anti-glypican 3 antibody.

BACKGROUND ART

The glypican family has been reported to be a novel family of heparan sulfate proteoglycans present on the cell surface. Five spieces of glypicans (glypican 1, glypican 2, glypican 3, glypican 4, and glypican 5) have been reported as members of the glypican family to date. The members of this family have a core protein of uniform size (approximately 60 kDa), share a unique and highly conserved sequence of cysteines, and are bound to the cell membrane via a glycosylphosphatidylinostiol (GPI) anchor.

Dally (division abnormally delayed) gene was identified by genetic screening of *Drosophila melanogaster* mutants that had an abnormal cell division pattern during the development of central nervous system. cDNA of Dally has been shown to have an open reading frame (ORF) that codes for a product that exhibits sequence homology (24 to 26% homology) with vertebrate integral membrane proteoglycans (GRIPs) having all the characteristics of glypicans. It was later suggested that Dally plays a role in regulating the dpp (decapentaplegia) receptor mechanism, suggesting the possibility that mammalian glypican modulates TGF and BMP signal transduction. That is, it has been suggested that glypican may function as a coreceptor for some heparin-binding growth factors (e.g., EGF, PDGF, BMP2, FGFs).

Glypican 3 was isolated as a developmentally regulated transcript from the rat small intestine (Filmus, J., Church, J. G., and Buick, R. N. (1988) *Mol. Cell. Biol.* 8, 4243-4249). It was thereafter identified as OCI-5, a GPI anchored type heparan sulfate proteoglycan of the glypican family having a core protein with a molecular weight of 69 kDa (Filmus, J., Shi, W., Wong, Z.-M., and Wong, M. J. (1995) *Biochem. J.* 311, 561-565). In humans, a gene encoding glypican 3 has also been isolated as MRX-7 from a human stomach cancer cell line (Hermann Lage et al., *Gene* 188 (1997) 151-156). Glypican 3 has been reported to form a protein-protein complex with insulin-like growth factor-2 and to regulate the action of this growth factor (Pilia, G. et al. (1996) *Nat. Genet.* 12, 241-247). This report suggests that glypican 3 does not necessarily interact with growth factors through the heparan sulfate chain.

It has also been reported that glypican 3 may possibly be utilized as a marker of hepatocellular carcinoma (Hey-Chi Hsu et al., *Cancer Research* 57, 5179-5184 (1997)). Also it has been reported that anti-glypican 3 antibody exhibits a cytotoxic activity against liver cancer cells and may be useful as an anti-cancer agent (WO 03/00883).

However, there have been no reports to the effect that it is possible to use anti-glypican 3 antibody for adjuvant therapy after a cancer treatment.

SUMMARY OF THE INVENTION

As a result of extensive and intensive investigations, the present inventors discovered that anti-glypican 3 antibody is useful for an adjuvant therapy following a cancer treatment and achieved this invention based on this discovery. In addition, they found that the recurrence of cancer can be prevented by the administration of anti-glypican 3 antibody at a stage after cancer treatment where cancer cells are not observed, and that anti-glypican 3 antibody is useful as an agent for preventing cancer and as an agent for preventing the recurrence of cancer.

DETAILED DESCRIPTION OF THE INVENTION

The present invention provides an anti-cancer agent comprising anti-glypican 3 antibody wherein the agent is administered after cancer treatment. After cancer treatment is preferably after the treatment of liver cancer. In particular the treatment of liver cancer is the resection of liver cancer cells. The anti-cancer agent according to the present invention is preferably administered in those cases where glypican 3 is expressed in the resected liver cancer cells. The anti-glypican 3 antibody is preferably a monoclonal antibody.

The anti-cancer agent according to the present invention is particularly useful in adjuvant therapy. Even in cases where it is believed that cancer treatment surgery has resulted in the removal of the cancer cells or their death, undetected cancer cells may still remain present. Cancer may recur after a certain period of time when such cancer cells remain present, and cancer treatment must therefore be followed by a treatment to prevent cancer recurrence. Such a treatment is known as adjuvant therapy or post-surgical adjuvant therapy.

Within the context of the present invention, cancer treatment refers to any treatment that has a goal including inhibiting the growth of cancer cells or killing cancer cells or decreasing cancer cells, such as resection of the cancer, chemotherapy using an anti-cancer agent, radiation therapy, percutaneous ethanol injection therapy, percutaneous radiofrequency thermal coagulation therapy, or transcatheter arterial embolization therapy. A preferred cancer treatment in the present invention is cancer resection. The concept of "post-cancer treatment" or "after cancer treatment" refers to after such treatments have been carried out. This concept of "post-cancer treatment" or "after cancer treatment" in the present invention does not necessarily mean that the cancer has been cured.

The anti-glypican 3 antibody according to the present invention may be administered to a post-cancer treatment patient after determining as to whether glypican 3 is expressed. Any method may be used to determine whether glypican 3 is being expressed. For example, the expression of glypican 3 protein can be determined using anti-glypican 3 antibody, while the expression of the glypican 3 gene can be determined by, for example, PCR.

The anti-glypican 3 antibody may be administered in any timing after cancer treatment, and administration may be carried out immediately after cancer treatment or after some interval of time. A preferred timing for administration in the present invention is in the interval from after cancer treatment up through cancer recurrence. In the case of post-surgical adjuvant therapy, administration is typically begun within 12 weeks or within 6 weeks after treatment. Recurrence of cancer can be diagnosed by methods known to those skilled in the art; for example, the occurrence of a tumor can be determined by visual findings or by pathological findings. The presence of a tumor can be confirmed by methods known to those skilled in the art, such as imaging or methods based on a tumor marker such as AFP.

Any cancer can be treated using the anti-cancer agent according to the present invention, including, but not limited to, liver cancer, lung cancer, colon cancer, breast cancer, prostate cancer, leukemia, lymphoma, pancreatic cancer, and bile duct cancer. Hepatocarcinoma is a cancer particularly well suited for treatment using the anti-cancer agent according to the present invention. The liver cancer may be primary or secondary cancer, which includes hepatocellular carcinoma, intrahepatic cholangiocarcinoma, bile duct cystadenocarcinoma, combined hepatocellular carcinoma and cholangiocarcinoma, hepatoblastoma, undifferentiated carcinoma, angiosarcoma, leiomyosarcoma of the liver, and undifferentiated sarcoma.

A particularly preferred embodiment of adjuvant therapy using the anti-cancer agent according to the present invention is the prevention of the recurrence of liver cancer by administering anti-glypican 3 antibody after the resection of liver cancer cells.

There are no particular requirements with regard to the origin, type (monoclonal or polyclonal), and form of the anti-glypican 3 antibody used in the present invention.

The anti-glypican 3 antibody used in the present invention can be obtained by a known means in the form of polyclonal or monoclonal antibody. Monoclonal antibody of mammalian origin is a particularly preferred anti-glypican 3 antibody for use in the present invention. Examples of monoclonal antibody of mammalian origin include antibody produced by hybridomas and antibody produced by a host that has been transformed by genetic engineering techniques with an expression vector containing the antibody gene.

A monoclonal antibody-producing hybridoma can be prepared substantially using known techniques as follows. A hybridoma can be prepared by immunization of an a animal according to a standard immunization method using glypican 3 as the sensitizing antigen; fusing the resulting immunocytes with known partner cells by a standard cell fusion technique; and then screening for monoclonal antibody-producing cells by a standard screening procedure.

In specific terms, monoclonal antibody can be prepared as follows. First, human glypican 3 for use as the sensitizing antigen for antibody production is obtained by inducing the expression of the glypican 3 (MXR7) according to the gene/amino acid sequence as disclosed by Lage, H. et al., *Gene* 188 (1997), 151-156. The gene sequence and amino acid sequence of glypican 3 are shown, respectively, in SEQ ID NO: 1 and SEQ ID NO: 2. Specifically, the gene sequence encoding glypican 3 is inserted in a known expression vector system; an appropriate host cell is transformed; and human glypican 3 protein of interest is subsequently purified by a known method from the host cell or the culture supernatant.

This purified glypican 3 protein is then used as the sensitizing antigen. Alternatively, a partial peptide of glypican 3 can be used as the sensitizing antigen. Such a partial peptide can be obtained by chemical synthesis of a peptide in accordance with the amino acid sequence of human glypican 3.

The anti-glypican 3 antibody will exhibit an anti-cancer activity through its cytotoxic activity such as ADCC or CDC. Also it will exhibit an anti-cancer activity by conjugating anti-glypican 3 antibody with a cytotoxic substance such as a radioisotope, a chemotherapeutic agent, or a bacteria-derived toxin. The epitope on the glypican 3 molecule that is recognized by the anti-glypican 3 antibody is not limited to a particular epitope. The anti-glypican 3 antibody may recognize any epitope that is present on the glypican 3 molecule. Accordingly, any peptide fragment containing an epitope present on the glypican 3 molecule can be used as the antigen for preparing the anti-glypican 3 antibody of the present invention.

The mammal to be immunized with the sensitizing antigen is not specifically limited and is preferably selected based on a consideration of the compatibility with the partner cell that will be used for cell fusion. For example, rabbits, monkeys, or rodents such as mice, rats, and hamsters are generally used.

The animal is immunized with the sensitizing antigen according to known techniques. For example, immunization can be carried out by a general method in which a mammal is injected intraperitoneally or subcutaneously with the sensitizing antigen. Specifically, the sensitizing antigen is diluted with or suspended in an appropriate volume of phosphate-buffered saline (PBS), physiological saline, or the like; an appropriate amount of a standard adjuvant such as Freund's complete adjuvant is admixed therewith as necessary; and the mixture is emulsified and administered to the mammal for a plurality of times every 4 to 21 days. In addition, an appropriate carrier may also be used during immunization with the sensitizing antigen.

A mammalian myeloma cell is used as the partner cell for fusion with the aforementioned immunocyte. Various known cell lines are suitably used as a myeloma cell, and include, for example, P3 (P3x63Ag8.653) (*J. Immunol.* (1979) 123, 1548-1550), P3x63Ag8U.1 (*Current Topics in Microbiology and Immunology* (1978) 81, 1-7), NS-1 (Kohler, G. and Milstein, C. *Eur. J. Immunol.* (1976) 6, 511-519), MPC-11 (Margulies, D. H. et al., *Cell* (1976) 8, 405-415), SP2/0 (Shulman, M. et al., *Nature* (1978) 276, 269-270), FO (de St. Groth, S. F. et al., *J. Immunol. Methods* (1980) 35, 1-21), S194 (Trowbridge, I. S. *J. Exp. Med.* (1978) 148, 313-323), and R210 (Galfre, G. et al., *Nature* (1979) 277, 131-133).

Immunocytes are fused with the myeloma cells substantially according to known procedures, for example, the procedure of Kohler and Milstein et al. (Kohler, G. and Milstein, C., *Methods Enzymol.* (1981) 73, 3-46).

More specifically, cell fusion is carried out in a standard nutrient culture medium in the presence of, for example, a cell-fusion promoter. For example, polyethylene glycol (PEG), Sendai virus (also known as hemagglutinating virus of Japan or HVJ), or the like may be used as the cell-fusion promoter. If desired, an auxiliary such as dimethyl sulfoxide can also be added in order to further enhance the fusion efficiency.

The immunocytes and myeloma cells may be mixed in any proportion. For example, it is preferable that the number of immunocytes be 1 to 10 times the number of myeloma cells. Examples of the culture medium used for the cell include, for example, RPMI1640 culture medium or MEM culture medium, which are particularly suitable for the growth of the aforementioned myeloma cell lines, and other standard culture media that are used to culture cells of this type. Also a serum supplement such as fetal calf serum (FCS) can be used in combination.

Cell fusion is carried out by thoroughly mixing prescribed amounts of the aforementioned immunocytes and myeloma cells in the aforementioned culture medium; adding a PEG (e.g., with an average molecular weight of approximately 1000 to 6000) solution with a concentration generally of 30 to 60% (w/v) that has been pre-heated to approximately 37° C.; and then mixing them to allow for formation of fused cells (hybridomas) of interest. Subsequently, a suitable medium is added and centrifuged to remove the supernatant. This process is repeated to remove the cell fusion agent and other materials unfavorable to the growth of the hybridoma.

The thus obtained hybridomas are then selected by culturing them in a standard selection culture medium such as HAT culture medium (culture medium containing hypoxanthine, aminopterin, and thymidine). Culture in this HAT culture medium is continued for a time period sufficient for cells (unfused cells) other than the desired hybridomas to die (normally several days to several weeks). A standard limiting dilution procedure is then carried out for screening and monocloning of the hybridoma that produces the desired antibody.

In addition to the aforementioned method of obtaining a hybridoma by immunizing a non-human animal with antigen, the desired human antibodies that exhibit a binding activity for glypican 3 can also be obtained by sensitizing human lymphocytes to glypican 3 in vitro and fusing the sensitized lymphocytes with human-derived myeloma cells that have a permanent division capacity (see Japanese Patent Publication No. Hei 1-59878). In addition, glypican 3 can be administered as an antigen to a transgenic animal having the complete repertoire of human antibody genes; anti-glypican 3 antibody-producing cells can subsequently be obtained; and human antibody against glypican 3 can be obtained from cells produced by immortalizing the anti-glypican 3 antibody-producing cells (see International Patent Publication Nos. WO 94/25585, WO 93/12227, WO 92/03918, and WO 94/02602).

The thus prepared monoclonal antibody-producing hybridoma can be serially cultured on a standard culture medium or can be stored long-term in liquid nitrogen.

Monoclonal antibodies can be obtained from the hybridoma by, for example, culturing the hybridoma by a standard method and recovering the monoclonal antibodies from the culture supernatant, or administrating and growing the hybridoma in a mammal compatible with the hybridoma and obtaining the monoclonal antibodies from the ascites fluid. The former method is suitable for obtaining antibody of high purity, while the latter method is suitable for the mass production of antibody.

The monoclonal antibody used in the present invention may be a recombinant monoclonal antibody prepared by genetic engineering techniques by cloning the antibody gene from the hybridoma, integrating the gene into an appropriate vector, introducing the vector into a host, and causing the host to produce the recombinant monoclonal antibody (e.g., see Vandamme, A. M. et al., Eur. J. Biochem. (1990) 192, 767-775, 1990).

Specifically, mRNA encoding the variable (V) region of an anti-glypican 3 antibody is isolated from a hybridoma that produces anti-glypican 3 antibody. The MRNA can be isolated by a known method, for example, by preparation of the total RNA by the guanidine ultracentrifugation method (Chirgwin, J. M. et al., Biochemistry (1979) 18, 5294-5299) or the AGPC method (Chomczynski, P. et al., Anal. Biochem. (1987) 162, 156-159), followed by preparation of the mRNA of interest using mRNA Purification Kit (Pharmacia) or the like. In addition, the mRNA can also be directly prepared using a QuickPrep mRNA Purification Kit (Pharmacia).

The cDNA of the antibody V region is synthesized from the thus obtained MRNA using reverse transcriptase. cDNA synthesis can be carried out using, for example, an AMV Reverse Transcriptase First-Strand cDNA Synthesis Kit (Seikagaku Corporation) or the like. cDNA synthesis and amplification can also be carried out, for example, by the 5'-RACE method using a 5'-Ampli FINDER RACE Kit (Clontech) and PCR (Frohman, M. A. et al., Proc. Natl. Acad. Sci. USA (1988) 85, 8998-9002, Belyavsky, A. et al., Nucleic Acids Res. (1989) 17, 2919-2932).

The target DNA fragment is purified from the thus obtained PCR product and then ligated into a vector DNA to prepare a recombinant vector. The vector is then introduced into, for example, E. coli; and colony selection yields the desired recombinant vector. The nucleotide sequence of the target DNA is then determined by a known method, such as the dideoxynucleotide chain termination method.

After the DNA encoding the V region of the target anti-glypican 3 antibody has been obtained, this DNA is integrated into an expression vector that contains DNA encoding the constant region (C region) of the desired antibody.

To produce the anti-glypican 3 antibody for use in the present invention, the antibody gene is integrated into an expression vector in such a manner that the gene is expressed under the control of an expression control region, for example, an enhancer and a promoter. Next, a host cell is transformed with the expression vector and expression of the antibody is induced.

The antibody gene can be expressed by integrating DNA encoding the antibody heavy chain (H-chain) and DNA encoding the antibody light chain (L-chain) separately into expression vectors and then simultaneously transforming a host cell with these vectors; or by integrating DNAs encoding the H-chain and the L-chain into a single expression vector and transforming a host cell with this vector (see WO 94/11523).

In addition to a host cell as described above, a transgenic animal can be used to produce recombinant antibody. For example, a fused gene can be prepared by inserting the antibody gene into a gene encoding a protein (e.g., goat β-casein) that will be produced in milk. A DNA fragment containing the fused gene with the inserted antibody gene is then injected into a goat embryo and the embryo is introduced into a female goat. The desired antibody can be obtained from the milk produced by the transgenic goat (or its progeny) born from the goat that has received the embryo. Furthermore, suitable hormones can be administered to the transgenic goat in order to increase the volume of milk produced by the transgenic goat that contains the desired antibody (Ebert, K. M. et al., Bio/Technology (1994) 12, 699-702).

In addition to the antibodies cited above, the present invention can make use of artificially modified genetically recombinant antibodies, such as chimeric antibodies and humanized antibodies, for the purpose of lowering the heteroantigenicity for humans. These modified antibodies can be produced by already known methods.

Chimeric antibodies can be obtained by ligating DNA encoding the antibody V region (obtained as described above) to DNA encoding the human antibody C region, integrating the product into an expression vector, and then introducing the vector into a host and inducing production. Chimeric antibodies useful for the present invention can be obtained by such already known methods.

Humanized antibodies, which are also referred to as reshaped human antibodies, are prepared by grafting an antibody complementarity determining region (CDR) from a non-human mammal, such as mouse, into the complementarity determining region of a human antibody. General gene recombination techniques for this procedure are also known in the art (see EP 125023 and WO 96/02576).

Specifically, a DNA sequence designed to link the CDR of a mouse antibody with the framework region (FR) of a human antibody is synthesized by PCR using as primers several oligonucleotides constructed to have regions that overlap the terminal regions of both the CDR and FR (see the method described in WO 98/13388).

A framework region in which the complementarity determining region forms an excellent antigen-binding site is selected for the human antibody framework region linked with the CDR regions. Amino acids in the framework region in the antibody variable region may be substituted as necessary in order that the complementarity determining region of the reshaped human antibody will form an appropriate antigen-binding site (Sato, K. et al., *Cancer Res*. (1993) 53, 851-856).

Human antibody C regions are used for the C regions of chimeric antibodies and humanized antibodies. For example, Cγ1, Cγ2, Cγ3, and Cγ4 can be used for the H-chain and Cκ and Cλ can be used for the L-chain. In addition, the human antibody C region may be modified in order to improve the stability of the antibody or its production process.

A chimeric antibody consists of the variable region of an antibody derived from a non-human mammal and a constant region derived from a human antibody, while a humanized antibody consists of a complementarity determining region of an antibody derived from a non-human mammal and a framework region and C region derived from a human antibody. Since the humanized antibody is designed to have a low antigenicity in humans, it is useful as an active ingredient in the therapeutic agent according to the present invention.

The antibody used in the present invention is not limited to the whole antibody molecule as long as it can bind to glypican 3 and inhibit the activity of glypican 3, and therefore encompasses antibody fragments and modifications thereof as well as divalent antibodies and monovalent antibodies. Examples of antibody fragments include Fab, F(ab')2, Fv, Fab/c having one Fab and a complete Fc, and single chain Fv (scFv) in which H-chain or L-chain Fv is linked by an appropriate linker. Specifically, an antibody fragment can be produced by treating an antibody with an enzyme such as papain or pepsin. Alternatively, a gene encoding such an antibody fragment can be constructed and introduced into expression vectors and expressed by appropriate host cells (see e.g., Co, M. S. et al., *J. Immunol*. (1994) 152, 2968-2976, Better, M. & Horwitz, A. H. *Methods in Enzymology* (1989) 178, 476-496, Academic Press, Inc., Plueckthun, A. & Skerra, A. *Methods in Enzymology* (1989) 178, 476-496, Academic Press, Inc., Lamoyi, E., *Methods in Enzymology* (1989) 121, 652-663, Rousseaux, J. et al., *Methods in Enzymology* (1989) 121, 663-669, and Bird, R. E. et al., *TIBTECH* (1991) 9, 132-137).

scFv is obtained by linking an antibody H-chain V region and L-chain V region. The H-chain V region and the L-chain V region are linked in scFv through a linker and preferably a peptide linker (Huston, J. S. et al., *Proc. Natl. Acad. Sci. U.S.A*. (1988) 85, 5879-5883). The H-chain V region and the L-chain V region of scFv may be derived from any of the antibodies described herein. The peptide linker linking the V regions can be, for example, any single-stranded peptide comprising 12 to 19 amino acid residues.

DNA encoding scFv can be obtained as follows. DNA encoding the H-chain or H-chain V region of the aforementioned antibody and DNA encoding the L-chain or L-chain V region are amplified by PCR using as templates DNA regions that encode all or desired amino acid sequences of the aforementioned sequences and primer pairs that specify both ends thereof. Then additional amplification is carried out with a combination of DNA encoding a peptide linker region and a primer pair that defines both ends to be ligated to the H-chain and L-chain.

In addition, once scFv-encoding DNA has been prepared, an expression vector containing this DNA and a host transformed with the expression vector can be obtained according to standard methods. The scFv can then be obtained by standard methods using such a host.

An antibody fragment can be produced by preparing a gene coding for the fragment and expressing it in a host in the same manner as described above. The term "antibody" as used herein also encompasses these antibody fragments.

Another example of a modified antibody used in the invention is anti-glypican antibody conjugated with any of various molecules, such as polyethylene glycol (PEG). The term "antibody" as used herein also encompasses these modified antibodies. Such a modified antibody can be prepared by chemically modifying an antibody obtained as above. Methods of antibody modification have already been established in the art.

The antibody used in the present invention may be a bispecific antibody. A bispecific antibody may have antigen-binding sites that recognize different epitopes on the glypican 3 molecule, or one antigen-binding site may recognize glypican 3 and the other antigen-binding site may recognize a cytotoxic substance such as a chemotherapeutic agent or cell-derived toxin. This enables the cytotoxic substance to directly act on a cell expressing glypican 3, thereby specifically damaging tumor cells and suppressing tumor cell proliferation. A bispecific antibody can be prepared by linking the H-L pairs of two types of antibodies. It can also be obtained by fusing hybridomas that produce different monoclonal antibodies to prepare bispecific antibody-producing fused cells. Bispecific antibodies can also be prepared by genetic engineering techniques.

An antibody gene constructed as described above can be expressed and obtained by known methods. In the case of mammalian cells, a gene can be expressed by functionally linking a commonly used effective promoter, the antibody gene to be expressed, and a polyA signal on its 3' downstream side. An example of the promoter/enhancer is human cytomegalovirus immediate early promoter/enhancer.

Examples of other promoter/enhancers that can be used in the present invention for expression of the antibody include, for example, viral promoter/enhancers from retrovirus, polyoma virus, adenovirus, or simian virus 40 (SV40), and promoter/enhancers derived from mammalian cells, such as human elongation factor 1α(HEF1α).

When an SV40 promoter/enhancer is used, gene expression can be readily carried out by the method of Mulligan et al. (*Nature* (1979) 277, 108), and when an HEF1α promoter/enhancer is used, gene expression can be readily carried out by the method of Mizushima et al. (*Nucleic Acids Res*. (1990) 18, 5322).

In the case of *E. coli*, gene expression can be achieved by functionally linking a commonly used effective promoter, a signal sequence for antibody secretion, and the antibody gene to be expressed. The promoter can be exemplified by the lacz promoter and the araB promoter. When the lacz promoter is used, expression can be achieved by the method of Ward et al.

(*Nature* (1998) 341, 544-546; *FASEB J.* (1992) 6, 2422-2427), and when the araB promoter is used, expression can be achieved by the method of Better et al. (*Science* (1988) 240, 1041-1043).

With regard to the signal sequence for antibody secretion, the pelB signal sequence (Lei, S. P. et al. *J. Bacteriol.* (1987) 169, 4379) may be used when the antibody is produced in the periplasm of *E. coli*. After the antibody produced in the periplasm has been isolated, the antibody structure is appropriately refolded for use.

The replication origin used in the invention includes, for example, those derived from SV40, polyoma virus, adenovirus, or bovine papilloma virus (BPV). In order to amplify the number of gene copies in the host cell system, the expression vector can contain, for example, the aminoglycoside transferase (APH) gene, thymidine kinase (TK) gene, *E. coli* xanthine guanine phosphoribosyltransferase (Ecogpt) gene, or dihydrofolate reductase (dhfr) gene as a selection marker.

Any expression system, for example, a eukaryotic cell system or a prokaryotic cell system, can be used to produce the antibody used in the present invention. Examples of eukaryotic cells include animal cells such as an established mammalian cell system or insect cell system and true filamentous fungus cells and yeast cells. Examples of prokaryotic cells include bacterial cells such as cells of *E. coli*.

The antibody used in the present invention is preferably expressed in mammalian cells such as CHO, COS, myeloma, BHK, Vero, or HeLa cells.

The transformed host cell is then cultured in vitro or in vivo to induce production of the antibody of interest. The host cell can be cultured according to known methods. For example, DMEM, MEM, RPMI1640, or IMDM can be used as the culture medium. A serum supplement such as fetal calf serum (FCS) can also be used.

Known means can be used to assay the antigen-binding activity of the antibody used in the present invention (*Antibodies A Laboratory Manual*. Ed Harlow, David Lane, Cold Spring Harbor Laboratory, 1988) and to measure its ligand-receptor binding inhibitory activity (Harada, A. et al., *International Immunology* (1993) 5, 681-690).

The antigen-binding activity of the anti-glypican 3 antibody used in the present invention can be measured using ELISA (enzyme-linked immunosorbent assay), EIA (enzyme immunoassay), RIA (radioimmunoassay), or a fluorescent antibody technique. In an enzyme immunoassay, for example, the antigen-binding activity can be evaluated by adding a sample containing the anti-glypican 3 antibody, such as the culture supernatant from anti-glypican 3 antibody-producing cells or the purified antibody, to a plate coated with glypican 3; adding a secondary antibody labeled with an enzyme such as alkaline phosphatase; incubating and then washing the plate; adding an enzyme substrate such as p-nitrophenyl phosphate; and measuring the absorbance. The cytotoxicity of the antibody used in the present invention can be measured by methods known to those skilled in the art.

The ADCC activity can be measured by mixing effector cells, target cells, and anti-glypican 3 antibody and then determining the level of ADCC. For example, mouse splenocytes or monocytes isolated from bone marrow or human peripheral blood can be used as the effector cells. Examples of a target cell include a human established cell line, such as the HuH-7 human hepatoma cell line. The ADCC activity can be measured by preliminarily labeling the target cells with $^{51}$Cr; adding anti-glypican 3 antibody to the cells; incubating the cells; then adding effector cells at an appropriate ratio with respect to the target cells; collecting the supernatant after incubation; and counting the radioactivity in the supernatant.

The CDC activity can be measured by mixing the aforementioned labeled target cells with anti-glypican 3 antibody; adding complement and incubating; and then counting the radioactivity in the supernatant.

Since an Fc region is generally required for an antibody to exert cytotoxicity, the anti-glypican 3 antibody used in the present invention preferably contains an Fc region in those cases where the cell growth inhibitor of the present invention utilizes the cytotoxic activity of the antibody.

The anti-cancer agent according to the present invention is used to prevent cancer or to prevent the recurrence of cancer after cancer treatment. The anti-cancer agent according to the present invention is particularly preferably used to prevent the recurrence of liver cancer after the resection of liver cancer cells.

The effective dose is selected from the range of 0.001 mg to 1000 mg per kg body weight per administration. Or, a dose can be selected from the range of 0.01 to 100000 mg/body per patient. However, effective dose of the anti-cancer agent according to the present invention containing anti-glypican 3 antibody is not limited to the above described doses.

The anti-cancer agent according to the present invention is generally administered by a parenteral route, for example, by injection (e.g., subcutaneous, intravenous, intramuscular, intraperitoneal) or a transdermal, transmucosal, nasal, or pulmonary route. It may also be administered orally.

With regard to the timing of administration of the anti-cancer agent according to the present invention, it can be administered either before or after the appearance of the clinical symptoms of the disease. According to a particularly preferred embodiment of the present invention, the anti-cancer agent according to the present invention can be administered as adjuvant therapy after the resection of liver cancer cells.

A therapeutic agent comprising the anti-glypican 3 antibody according to the present invention as an active ingredient can be formulated by standard methods (*Remington's Pharmaceutical Science*, latest edition, Mark Publishing Company, Easton, U.S.A.) and may contain pharmaceutically acceptable carriers and additives.

These carriers and pharmaceutical additives may include water, pharmaceutically acceptable organic solvents, collagen, polyvinyl alcohol, polyvinylpyrrolidone, carboxyvinyl polymer, sodium carboxymethyl cellulose, sodium polyacrylate, sodium alginate, water-soluble dextran, sodium carboxymethyl starch, pectin, methyl cellulose, ethyl cellulose, xanthan gum, gum arabic, casein, agar, polyethylene glycol, diglycerin, glycerin, propylene glycol, vaseline, paraffin, stearyl alcohol, stearic acid, human serum albumin (HSA), mannitol, sorbitol, lactose, and a surfactant acceptable as a pharmaceutical additive.

Such an additive or additives may be appropriately selected according to the dosage form of the therapeutic agent of the present invention, but is not limited to those listed above. For example, an injectable formulation can be prepared by dissolving purified anti-glypican 3 antibody in a solvent such as physiological saline, buffer, or a glucose solution, and then adding an adsorption inhibitor such as Tween 80, Tween 20, gelatin, or human serum albumin to the solution. Or, the freeze-dried agent may be used to prepare a dosage form, which is reconstituted by dissolution prior to use. Examples of the excipient used for freeze-drying include sugar alcohols and saccharides such as mannitol and glucose.

The content of all the patents and references expressly cited in this application are incorporated herein by reference in its entirety. Moreover, the content of the Description and Drawings of Japanese Patent Applications 2004-244273 and 2005-

90945, which are the basis for the priority claiming of this application, are incorporated herein by reference in its entirety.

EXAMPLES

The present invention is described in greater detail by the examples provided below, but these examples do not limit the scope of the present invention.

Example 1

Efficacy of Mouse Anti-Human Glypican 3 Antibody GC33 in Intrahepatic Transplant Mouse Model (1) Measurement of α-fetoprotein (AFP)

The serum concentration of human AFP was measured as a tumor marker using an ELISA kit for measurement of human AFP (Hope Laboratories). The detection limit by ELISA is about 1 ng/mL, and samples below the detection limit were taken to be 1 ng/mL. To obtain the serum, blood was collected in a Separapit S (Sekisui Chemical) by orbital blood collection, allowed to stand for 15 minutes at room temperature, and then centrifuged for 20 minutes at 1200×g.

(2) Preparation of Intrahepatic Transplant Mouse Model

An intrahepatic transplant mouse model was prepared as follows. HepG2 cells (ATCC) were adjusted to $1\times10^8$/mL using Hanks medium (Sigma). Under nembutal anesthesia, 50 µl of the HepG2 cell suspension ($5\times10^6$/mouse) was injected within the liver capsule of nude mice (Charles River). The serum AFP concentration was measured on day 21 post-transplant, and animals with the range of 10-100 ng/mL were divided into two groups (n=4). At this time point, the liver cancer cells (tumor mass) were not observed visually. These animals represent a model bearing intrahepatic micrometastasis surviving after liver resection.

(3) Antibody Administration

The administration formulation was prepared on the day of administration by diluting mouse anti-human glypican 3 antibody GC33 (refer to the Reference Example below) to 0.5 mg/mL in physiological saline (Otsuka Pharmaceutical). The formulation was administered to the aforementioned mouse model at 10 mL/kg through the tail vein on the 21st and 28th days following tumor transplantation. The physiological saline vehicle was administered in the same manner for the negative control.

(4) Evaluation of Antitumor Effect

Figure 1:
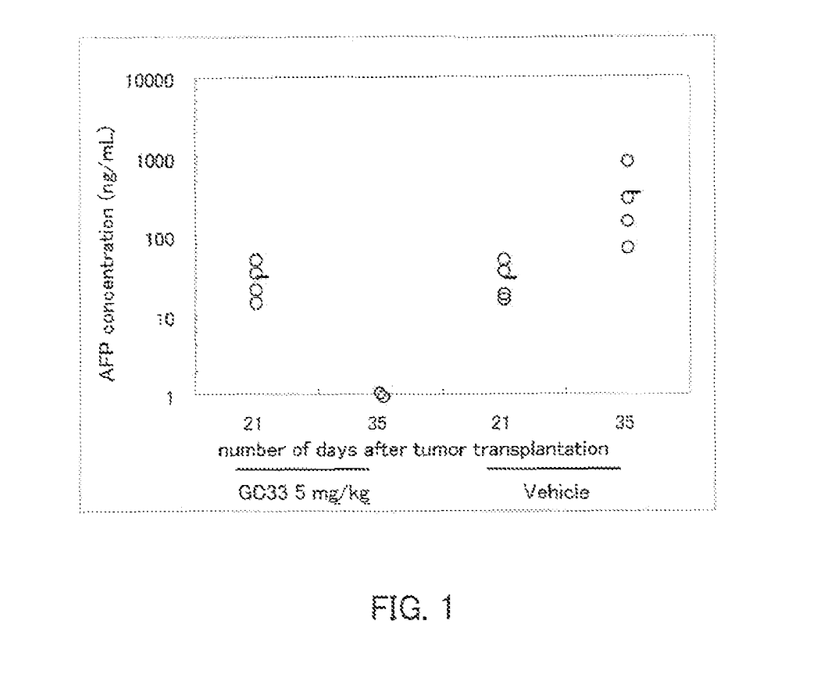
FIG. 1 is a graph showing the effect of the anti-cancer agent according to the present invention when administered to an intrahepatically transplanted mouse model.

The antitumor effect was evaluated based on the AFP concentration on the 35th day post-tumor transplantation. As shown in FIG. 1, the AFP concentration on the 35th day post-tumor transplant was lower for the group receiving GC33 than for the group receiving vehicle, indicating that the antibody of the invention has an anti-tumor effect.

As shown in the above results, GC33 exhibited an antitumor effect in the intrahepatic transplant model, suggesting that the antibody of the invention is useful in adjuvant therapy.

Example 2

Test of Early Administration of Mouse Anti-Human Glypican 3 Antibody GC33 in Intrahepatic Transplant Mouse Model (1) Measurement of α-fetoprotein (AFP)

The serum concentration of human AFP was measured as a tumor marker using an ELISA kit for measurement of human AFP (Hope Laboratories). The detection limit by ELISA is about 1 ng/mL, and samples below the detection limit were taken to be 1 ng/mL. To obtain the serum, blood was collected in a Separapit S (Sekisui Chemical) by orbital blood collection, allowed to stand for 15 minutes at room temperature, and then centrifuged for 20 minutes at 1200×g.

(2) Preparation of Intrahepatic Transplant Mouse Model

An intrahepatic transplant mouse model was prepared as follows. HepG2 cells (ATCC) were adjusted to $1\times10^8$/mL using Hanks medium (Sigma). Under nembutal anesthesia, 50 µL of the HepG2 cell suspension ($5\times10^6$/mouse) was injected within the liver capsule of nude mice (Charles River). On the day following transplantation, the animals were randomly divided into two groups (n=10). While HepG2 was present in the mouse liver on the day following transplantation, human AFP was not detected in the mouse serum at that time. These animals represent a clinically closer model bearing intrahepatic micrometastasis remaining after liver resection.

(3) Antibody Administration

The administration formulation was prepared on the day of administration by diluting mouse anti-human glypican 3 antibody GC33 (refer to the Reference Example below) to 0.5 mg/mL in physiological saline (Otsuka Pharmaceutical). The formulation was administered to the aforementioned mouse model at 10 mL/kg through the tail vein on the day following tumor transplantation and on the 7th day following tumor transplantation. The physiological saline vehicle was administered in the same manner for the negative control.

(4) Evaluation of Antitumor Effect

Figure 2:
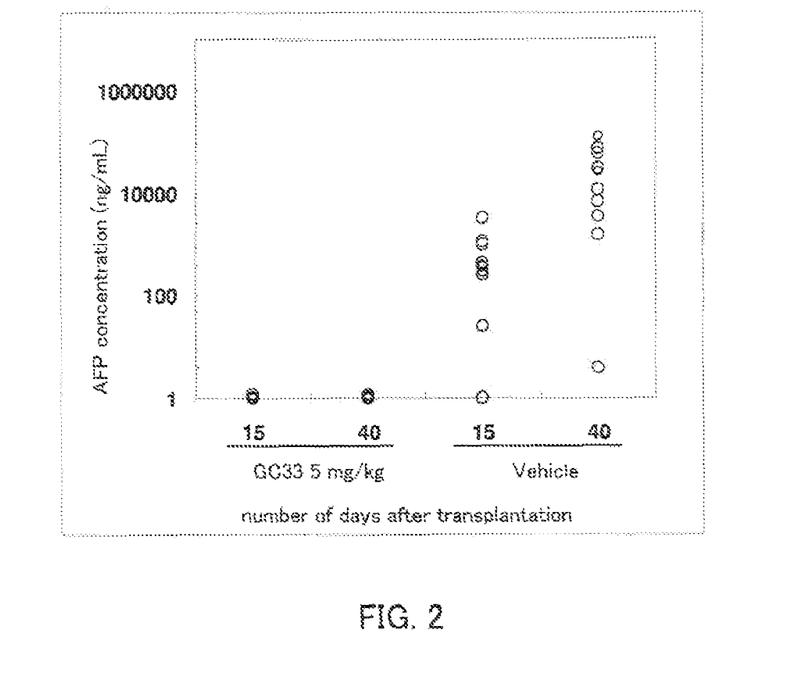
FIG. 2 is a graph showing the effect of the anticancer agent according to the present invention when administered at an early stage to an intrahepatically transplanted mouse model.

The antitumor effect was evaluated based on the AFP concentration on the 15th and 40th day post-tumor transplantation. As shown in FIG. 2, an increase in the APP concentration was not seen for either time point in the group receiving GC33. In contrast, an increase in AFP concentration was observed in the group receiving the vehicle.

As shown in the above results, tumor growth was also inhibited in a model in which liver cancer cells were intrahepatically transplanted, by administrating mouse anti-human glypican 3 antibody GC33 from an early stage where AFP was not detected, indicating that the antibody of the present invention is useful in adjuvant therapy.

Reference Example

Preparation of Mouse Anti-Human Glypican 3 Antibody GC33

Using as immunogen a fusion protein (GC-3) from GST and the peptide from the alanine at position 524 to the lysine at position 563 of glypican 3, three Balb/c mice (purchased from Charles River Japan) and three MRL/lpr mice were immunized. In the initial immunization, the emulsion prepared with FCA and adjusted to 100 µg GC-3 per head was administered subcutaneously. After two weeks, an emulsion prepared with FIA and adjusted to 50 µg per head was administered subcutaneously. After the fifth immunization, 50 μg per head was injected into the tail vein of all the mice as a final immunization, and then cell fusion was carried out. The hybridoma was screened by ELISA using immunoplates on which soluble GPC3 core protein (the hydrophobic region from amino acid 564 to 580 on the C-terminal side are deleted) had been immobilized. Positive clones were selected and monocloned by the limiting dilution method. In this way, the antibody GC33 exhibiting a strong binding activity for GPC3 was obtained. The amino acid sequence of the H-chain and L-chain variable regions of GC33 is shown in SEQ ID NO: 3 and SEQ ID NO: 4, respectively.

INDUSTRIAL APPLICABILITY

The anti-cancer agent according to the present invention is useful for preventing cancer and for preventing the recurrence of cancer.

The invention claimed is:

1. A method of preventing recurrence of liver cancer in a patient after a liver cancer treatment, the method comprising
identifying a patient who has undergone a previous liver cancer treatment; and
administering to the patient a composition comprising a monoclonal anti-glypican 3 antibody, wherein the antibody comprises the complementarity determining regions (CDRs) of the heavy chain variable region as set forth in SEQ ID NO:3 and the CDRs of the light chain variable region as set forth in SEQ ID NO:4.

2. The method according to claim 1, wherein the liver cancer is hepatocellular carcinoma.

3. The method according to claim 1, wherein the previous liver cancer treatment was a resection of liver cancer cells.

4. The method according to claim 3, wherein glypican 3 is expressed in the resected liver cancer cells.

5. The method according to claim 1, wherein the antibody is a humanized antibody.

6. A method of preventing recurrence of liver cancer in a patient after a liver cancer treatment, the method comprising
identifying a patient who has undergone a previous liver cancer treatment; and
administering to the patient a composition comprising a monoclonal anti-glypican 3 antibody, wherein the antibody comprises a heavy chain variable region comprising the sequence set forth in SEQ ID NO:3.

7. The method of claim 6, wherein the antibody further comprises a light chain variable region comprising the sequence set forth in SEQ ID NO:4.

8. The method according to claim 6, wherein the liver cancer is hepatocellular carcinoma.

9. The method according to claim 6, wherein the previous liver cancer treatment was a resection of liver cancer cells.

10. The method according to claim 9, wherein glypican 3 is expressed in the resected liver cancer cells.

11. The method according to claim 6, wherein the antibody is a chimeric antibody.

12. The method according to claim 7, wherein the antibody is a chimeric antibody.

13. The method according to claim 7, wherein the liver cancer is hepatocellular carcinoma.

14. The method according to claim 7, wherein the previous liver cancer treatment was a resection of liver cancer cells.

15. The method according to claim 14, wherein glypican 3 is expressed in the resected liver cancer cells.

16. A method of preventing recurrence of liver cancer in a patient after a liver cancer treatment, the method comprising
identifying a patient who has undergone a previous liver cancer treatment; and
administering to the patient a composition comprising a monoclonal anti-glypican 3 antibody, wherein the antibody comprises a light chain variable region comprising the sequence set forth in SEQ ID NO:4.

17. The method according to claim 16, wherein the liver cancer is hepatocellular carcinoma.

18. The method according to claim 16, wherein the previous liver cancer treatment was a resection of liver cancer cells.

19. The method according to claim 18, wherein glypican 3 is expressed in the resected liver cancer cells.

20. The method according to claim 16, wherein the antibody is a chimeric antibody.

* * * * *

SEQUENCE LISTING

<160> NUMBER OF SEQ ID NOS: 4

<210> SEQ ID NO 1
<211> LENGTH: 1743
<212> TYPE: DNA
<213> ORGANISM: Homo sapiens

<400> SEQUENCE: 1

```
atggccggga ccgtgcgcac cgcgtgcttg gtggtggcga tgctgctcag cttggacttc      60
ccgggacagg cgcagccccc gccgccgccg ccggacgcca cctgtcacca agtccgctcc     120
ttcttccaga gactgcagcc cggactcaag tgggtgccag aaactcccgt gccaggatca     180
gatttgcaag tatgtctccc taagggccca acatgctgct caagaaagat ggaagaaaaa     240
taccaactaa cagcacgatt gaacatggaa cagctgcttc agtctgcaag tatggagctc     300
aagttcttaa ttattcagaa tgctgcggtt ttccaagagg cctttgaaat tgttgttcgc     360
catgccaaga actacaccaa tgccatgttc aagaacaact acccaagcct gactccacaa     420
gcttttgagt ttgtgggtga attttcaca gatgtgtctc tctacatctt gggttctgac     480
atcaatgtag atgacatggt caatgaattg tttgacagcc tgtttccagt catctatacc     540
cagctaatga acccaggcct gcctgattca gccttggaca tcaatgagtg cctccgagga     600
gcaagacgtg acctgaaagt atttgggaat ttccccaagc ttattatgac ccaggtttcc     660
aagtcactgc aagtcactag gatcttcctt caggctctga tcttggaat tgaagtgatc     720 aacacaactg atcacctgaa gttcagtaag gactgtggcc gaatgctcac cagaatgtgg     780
tactgctctt actgccaggg actgatgatg gttaaaccct gtggcggtta ctgcaatgtg     840
gtcatgcaag gctgtatggc aggtgtggtg gagattgaca agtactggag agaatacatt     900
ctgtcccttg aagaacttgt gaatggcatg tacagaatct atgacatgga gaacgtactg     960
cttggtctct tttcaacaat ccatgattct atccagtatg tccagaagaa tgcaggaaag    1020
ctgaccacca ctattggcaa gttatgtgcc cattctcaac aacgccaata tagatctgct    1080
tattatcctg aagatctctt tattgacaag aaagtattaa aagttgctca tgtagaacat    1140
gaagaaacct tatccagccg aagaagggaa ctaattcaga gttgaagtc tttcatcagc    1200 ttctatagtg ctttgcctgg ctacatctgc agccatagcc ctgtggcgga aaacgacacc    1260
ctttgctgga tggacaaga actcgtggag agatacagcc aaaaggcagc aaggaatgga    1320
atgaaaaacc agttcaatct ccatgagctg aaaatgaagg gccctgagcc agtggtcagt    1380
caaattattg acaaactgaa gcacattaac cagctcctga gaaccatgtc tatgcccaaa    1440
ggtagagttc tggataaaaa cctggatgag gaagggtttg aaagtggaga ctgcggtgat    1500
gatgaagatg agtgcattgg aggctctggt gatggaatga taaaagtgaa gaatcagctc    1560
cgcttccttg cagaactggc ctatgatctg gatgtggatg atgcgcctgg aaacagtcag    1620
caggcaactc cgaaggacaa cgagataagc accttttcaca acctcgggaa cgttcattcc    1680
```

```
ccgctgaagc ttctcaccag catggccatc tcggtggtgt gcttcttctt cctggtgcac    1740
tga                                                                   1743
```

<210> SEQ ID NO 2
<211> LENGTH: 580
<212> TYPE: PRT
<213> ORGANISM: Homo sapiens

<400> SEQUENCE: 2

```
Met Ala Gly Thr Val Arg Thr Ala Cys Leu Val Val Ala Met Leu Leu
1               5                   10                  15

Ser Leu Asp Phe Pro Gly Gln Ala Gln Pro Pro Pro Pro Pro Pro Asp
                20                  25                  30

Ala Thr Cys His Gln Val Arg Ser Phe Phe Gln Arg Leu Gln Pro Gly
            35                  40                  45

Leu Lys Trp Val Pro Glu Thr Pro Val Pro Gly Ser Asp Leu Gln Val
        50                  55                  60

Cys Leu Pro Lys Gly Pro Thr Cys Cys Ser Arg Lys Met Glu Glu Lys
65                  70                  75                  80

Tyr Gln Leu Thr Ala Arg Leu Asn Met Glu Gln Leu Leu Gln Ser Ala
                85                  90                  95

Ser Met Glu Leu Lys Phe Leu Ile Ile Gln Asn Ala Ala Val Phe Gln
            100                 105                 110

Glu Ala Phe Glu Ile Val Val Arg His Ala Lys Asn Tyr Thr Asn Ala
        115                 120                 125

Met Phe Lys Asn Asn Tyr Pro Ser Leu Thr Pro Gln Ala Phe Glu Phe
130                 135                 140

Val Gly Glu Phe Phe Thr Asp Val Ser Leu Tyr Ile Leu Gly Ser Asp
145                 150                 155                 160

Ile Asn Val Asp Asp Met Val Asn Glu Leu Phe Asp Ser Leu Phe Pro
                165                 170                 175

Val Ile Tyr Thr Gln Leu Met Asn Pro Gly Leu Pro Asp Ser Ala Leu
            180                 185                 190

Asp Ile Asn Glu Cys Leu Arg Gly Ala Arg Arg Asp Leu Lys Val Phe
        195                 200                 205

Gly Asn Phe Pro Lys Leu Ile Met Thr Gln Val Ser Lys Ser Leu Gln
210                 215                 220

Val Thr Arg Ile Phe Leu Gln Ala Leu Asn Leu Gly Ile Glu Val Ile
225                 230                 235                 240

Asn Thr Thr Asp His Leu Lys Phe Ser Lys Asp Cys Gly Arg Met Leu
                245                 250                 255

Thr Arg Met Trp Tyr Cys Ser Tyr Cys Gln Gly Leu Met Met Val Lys
            260                 265                 270

Pro Cys Gly Gly Tyr Cys Asn Val Val Met Gln Gly Cys Met Ala Gly
        275                 280                 285

Val Val Glu Ile Asp Lys Tyr Trp Arg Glu Tyr Ile Leu Ser Leu Glu
290                 295                 300

Glu Leu Val Asn Gly Met Tyr Arg Ile Tyr Asp Met Glu Asn Val Leu
305                 310                 315                 320

Leu Gly Leu Phe Ser Thr Ile His Asp Ser Ile Gln Tyr Val Gln Lys
                325                 330                 335

Asn Ala Gly Lys Leu Thr Thr Thr Ile Gly Lys Leu Cys Ala His Ser
            340                 345                 350
```

```
Gln Gln Arg Gln Tyr Arg Ser Ala Tyr Tyr Pro Glu Asp Leu Phe Ile
            355                 360                 365

Asp Lys Lys Val Leu Lys Val Ala His Val Glu His Glu Glu Thr Leu
        370                 375                 380

Ser Ser Arg Arg Arg Glu Leu Ile Gln Lys Leu Lys Ser Phe Ile Ser
385                 390                 395                 400

Phe Tyr Ser Ala Leu Pro Gly Tyr Ile Cys Ser His Ser Pro Val Ala
                405                 410                 415

Glu Asn Asp Thr Leu Cys Trp Asn Gly Gln Glu Leu Val Glu Arg Tyr
            420                 425                 430

Ser Gln Lys Ala Ala Arg Asn Gly Met Lys Asn Gln Phe Asn Leu His
        435                 440                 445

Glu Leu Lys Met Lys Gly Pro Glu Pro Val Val Ser Gln Ile Ile Asp
    450                 455                 460

Lys Leu Lys His Ile Asn Gln Leu Leu Arg Thr Met Ser Met Pro Lys
465                 470                 475                 480

Gly Arg Val Leu Asp Lys Asn Leu Asp Glu Glu Gly Phe Glu Ser Gly
                485                 490                 495

Asp Cys Gly Asp Asp Glu Asp Glu Cys Ile Gly Gly Ser Gly Asp Gly
            500                 505                 510

Met Ile Lys Val Lys Asn Gln Leu Arg Phe Leu Ala Glu Leu Ala Tyr
        515                 520                 525

Asp Leu Asp Val Asp Asp Ala Pro Gly Asn Ser Gln Gln Ala Thr Pro
    530                 535                 540

Lys Asp Asn Glu Ile Ser Thr Phe His Asn Leu Gly Asn Val His Ser
545                 550                 555                 560

Pro Leu Lys Leu Leu Thr Ser Met Ala Ile Ser Val Val Cys Phe Phe
                565                 570                 575

Phe Leu Val His
            580

<210> SEQ ID NO 3
<211> LENGTH: 115
<212> TYPE: PRT
<213> ORGANISM: Mus musculus

<400> SEQUENCE: 3

Gln Val Gln Leu Gln Gln Ser Gly Ala Glu Leu Val Arg Pro Gly Ala
1               5                   10                  15

Ser Val Lys Leu Ser Cys Lys Ala Ser Gly Tyr Thr Phe Thr Asp Tyr
            20                  25                  30

Glu Met His Trp Val Lys Gln Thr Pro Val His Gly Leu Lys Trp Ile
        35                  40                  45

Gly Ala Leu Asp Pro Lys Thr Gly Asp Thr Ala Tyr Ser Gln Lys Phe
    50                  55                  60

Lys Gly Lys Ala Thr Leu Thr Ala Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ala
        115

<210> SEQ ID NO 4
```

```
<211> LENGTH: 112
<212> TYPE: PRT
<213> ORGANISM: Mus musculus

<400> SEQUENCE: 4

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr His Val Pro Pro Thr Phe Gly Ser Gly Thr Lys Leu Glu Ile Lys
            100                 105                 110
```